United States Patent
Lia et al.

(10) Patent No.: US 6,796,186 B2
(45) Date of Patent: Sep. 28, 2004

(54) BLOOD PRESSURE MEASURING DEVICE WITH DIRECTLY COUPLABLE MEASUREMENT MECHANISM

(75) Inventors: Raymond A. Lia, Auburn, NY (US); Robert L. Vivenzio, Auburn, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 0 days.

(21) Appl. No.: 10/608,202

(22) Filed: Jun. 27, 2003

(65) Prior Publication Data

US 2004/0083816 A1 May 6, 2004

Related U.S. Application Data

(60) Division of application No. 09/929,501, filed on Aug. 14, 2001, now Pat. No. 6,615,666, which is a continuation-in-part of application No. 09/669,474, filed on Sep. 25, 2000, now Pat. No. 6,422,086.

(51) Int. Cl.[7] .................................................. G01L 7/00
(52) U.S. Cl. ........................................................ 73/756
(58) Field of Search .......................... 73/715–727, 756; 600/485–488

(56) References Cited

U.S. PATENT DOCUMENTS

| | | |
|---|---|---|
| 1,106,341 A | 8/1914 | Bristol |
| 1,328,876 A | 1/1920 | Hill |
| 1,377,032 A | 5/1921 | Starling et al. |
| 2,087,494 A | 7/1937 | Annin |
| 2,341,137 A | 2/1944 | Damron |
| 2,564,669 A | 8/1951 | Brady |
| 2,636,394 A | 4/1953 | Melchior |
| 3,797,315 A | 3/1974 | Halpern |
| 3,805,618 A | 4/1974 | Csaposs et al. |
| 3,874,242 A | 4/1975 | Csaposs et al. |
| 4,036,061 A | 7/1977 | Speidel |
| 4,040,298 A | 8/1977 | Lee et al. |
| 4,255,970 A | 3/1981 | Van Pottelberg |
| 4,543,824 A | 10/1985 | Marterer |
| 4,685,336 A | 8/1987 | Lee |
| 5,181,422 A | 1/1993 | Leonard et al. |
| 5,753,821 A | 5/1998 | Chou |
| 5,966,829 A | 10/1999 | Lia et al. |
| 6,120,458 A | 9/2000 | Lia et al. |
| 6,168,566 B1 | 1/2001 | Lia et al. |
| 6,213,953 B1 * | 4/2001 | Reeves ....................... 600/499 |
| 6,234,972 B1 * | 5/2001 | Lia et al. .................... 600/485 |
| 6,615,666 B1 * | 9/2003 | Lia et al. ...................... 73/715 |

FOREIGN PATENT DOCUMENTS

| | | |
|---|---|---|
| DE | 0 591 564 A1 | 10/1992 |
| EP | 0 705 563 A | 4/1996 |
| FR | 2592297 A | 7/1987 |
| WO | 00 22983 A | 4/2000 |
| WO | 00/40941 | 7/2000 |

* cited by examiner

Primary Examiner—William Oen
(74) Attorney, Agent, or Firm—Wall Marjama & Bilinski LLP

(57) ABSTRACT

A pressure measuring device includes a housing which retains a pressure responsive element interconnected to an indicating member that moves relative to a dial face when a change of pressure is detected. A peripheral bumper is mounted to the housing exterior, the bumper including an extending portion which creates a discontinuous path for shock or impact loads applied to the bumper relative to a continual movement mechanism. The housing can further include a discontinuous region imposed in an engagement portion of the housing, the engagement portion permitting the housing to be directly attached to an inflatable blood pressure sleeve.

13 Claims, 13 Drawing Sheets

BLOOD PRESSURE MEASURING DEVICE WITH DIRECTLY COUPLABLE MEASUREMENT MECHANISM

CROSS REFERENCE TO RELATED APPLICATION

This application is a divisional (DIV) application of U.S. Ser. No. 09/929,501, filed Aug. 14, 2001, now U.S. Pat. No. 6,615,666 and entitled: PRESSURE MEASURING DEVICE which is a continuation in part (CIP) of U.S. Ser. No. 09/669,474 (U.S. Pat. No. 6,422,086 issued Jul. 23, 2002) filed Sep. 25, 2000.

FIELD OF THE INVENTION

The invention relates to the field of measuring instruments, and more particularly to a shock-resistant gage housing for a pressure measuring device such as a sphygmomanometer.

BACKGROUND OF THE INVENTION

Pressure measuring devices such as sphygmomanometers, which are used to measure the arterial blood pressure of a patent, typically include a pneumatic bulb which inflates a pressure chamber of an attached sleeve that is fitted over a limb (i.e., an arm or a leg) of the patient. A diaphragm or bellows assembly, responsive to changes in fluid pressure of the pneumatic bulb and the sleeve pressure chamber, is positioned in a gage housing which is fluidly connected to the pressure chamber of the sleeve through flexible tubes or hoses. A pointer of a dial indicator is interconnected to the bellows assembly through a movement mechanism which is retained within the gage housing, whereby inflation of the bellows causes corresponding circumferential movement of the pointer enabling a blood pressure measurement procedure to be carried out by a caregiver.

Typically, the above referred to movement mechanisms are quite intricate and complex, and are akin in terms of their manufacture and precision to Swiss watches. For example, and in one such movement mechanism, a pair of diaphragm springs are attached adjacent opposing ends of a spindle. A bottom end of the spindle is placed in contact with the bellows assembly and a twisted bronze band perpendicularly disposed at the top end of the spindle is connected in parallel by a horizontally disposed spring bent part. As the spindle deflects axially in response to the inflation of the bellows, the bent spring part is also caused to deflect, thereby causing the band to twist. The pointer, attached to the bronze band, therefore is caused to rotate in relation to an adjacent dial face.

Devices, such as the foregoing, include numerous moving and relatively complex components, some or each of having numerous bearing surfaces. Therefore, such known devices must be manufactured with relatively strict tolerance margins and significant associated costs in terms of both precision and failure rate in order to minimize errors.

In addition, any adjustments required after assembly of the above mechanisms, such as to null the pointer or adjust the sensitivity of the device, require substantial tear down or at least same undesired disassembly.

Furthermore, discrete and separate elements are typically required within the instrument housing for independently supporting the movement mechanism and the bellows assembly, respectively, and for defining an expansion chamber for the bellows assembly there between.

A more recent and simplified movement mechanism is described in U.S. Pat. No. 5,996,829, incorporated by reference in its entirety. The mechanism includes a vertically disposed axial cartridge having a spirally wrapped ribbon spring with one end mounted to an axially movable elongate shaft and the remaining end of the spring being attached to a fixed tubular sleeve. A bottom portion of the elongate shaft is positioned relative to an expandable diaphragm or bellows, wherein subsequent axial translation of the shaft, caused by movement of the diaphragm, elongates the spirally wound ribbon spring and produces repeatable circumferential movement of a pointer supported at the top end of the shaft. The above movement mechanism is far more lightweight than those previously known due to its simplified construction.

A further advance, described in U.S. Pat. No. 6,168,566, also incorporated by reference in its entirety, permits the design of a housing retaining the movement mechanism described in the '829 patent to be far more compact.

In spite of the advancements described herein for making pressure measuring devices lighter and less complex in terms of their manufacture, there is still a corresponding need to improve the overall reliability of such devices, particularly with regard to their ability to withstand impact or shock loading. That is to say, if a gage housing for a blood pressure measuring device were to be dropped during use, it is nearly a certainty that the gage housing would be damaged severely enough to prevent further use of the device.

SUMMARY OF THE INVENTION

It is a primary object of the present invention to overcome the above-noted deficiencies of the prior art.

It is yet another primary object of the present invention to provide a pressure measuring device which is much more resistant to shock and impact forces than those previously known in the field.

A pressure measuring device, said device comprising:

a housing;

at least one pressure responsive element disposed within said housing;

a movement mechanism having an input end in proximity to a moveable surface of said at least one pressure responsive element;

an indicator connected to an output end of said movement mechanism which indicates changes in pressure; and shock absorbing means for preventing the transmission of certain shock and impact loads to said device, said shock absorbing means including means for creating a noncontinuous path in order to prevent impinging said shock and input loads from reaching the components contained within the housing.

According to another preferred aspect of the invention, there is provided a pressure measuring device including a housing, said housing retaining a pressure responsive element which is connected to an indicating member that moves relative to a dial face, said device further including a peripheral bumper mounted to said housing, said bumper including an extending portion creating a discontinuous path for a shock or impact load applied to said bumper relative to a movement mechanism retained within said housing.

An advantage of the present invention is that a housing as described herein, such as for use with a blood pressure measuring device, can be dropped or otherwise subjected to shock or impact loads in situations which could be actually encountered during use with minimal damage to the mechanism contained in the housing.

Another advantage of the present invention is that the shock resistant features described herein do not add significant weight to the housing nor detract from the overall reliability or operation of the pressure measuring device.

Yet another advantage of the present invention is that the shock resistant features can easily be manufactured or incorporated into an existing pressure measuring device without significant impacts involving either cost or time.

Still another advantage of the present invention is that other gage housings which can by virtue of an aspect of the present invention be configured for direct connection to a blood pressure sleeve can also include shock resistant features as described herein.

These and other objects, features, and advantages will be more readily apparent to one of ordinary skill in the field from the following Detailed Description which should be read in conjunction with the accompanying drawings.

BRIEF DESCRIPTION OF THE DRAWINGS

FIG. 9A is an enlarged view of the attachment of the peripheral bumper to the gage housing of FIG. 9;

FIGS. 12A and 12B are enlarged partial sectioned views of a protective peripheral bumper as attached to the gage housing of FIG. 12;

DETAILED DESCRIPTION

The present invention is herein described with reference to several preferred embodiments, each of which specifically relates to blood pressure measuring apparatus. However, it should be evident to one of sufficient skill in the field that certain other variations and modifications could be made utilizing the inventive concepts described herein, as well as alternate applications other than blood pressure measurement, including use in barometers, pressure vessel indicators, pressure sensitive switches, valves, and literally any industrial or medical device requiring a pressure responsive element. Furthermore and throughout the course of the following discussion, terms such as "upwardly", "downwardly", "upper", "lower", "top", "bottom", "vertically", "horizontally" and the like are used to provide a frame of reference with regard to the accompanying drawings. These terms, however, should not be treated as limiting with regard to the invention as described herein. In addition, a number of terms are used herein which require definitions. "Gearless" as used herein refers to any movement mechanism disposed within a gage housing which does not include a gear or gear-like element. The primary embodiments referred to throughout the majority of the following discussion refer to a gearless analog blood pressure measurement apparatus.

"Hoseless" as used herein refers to a direct connection between a gage housing and an inflatable sleeve of a pressure measuring apparatus without any intermediate hose or hoses there between. Several preferred embodiments of hoseless attachments for a blood pressure measuring apparatus are described throughout the course of the following discussion.

Figure 1:
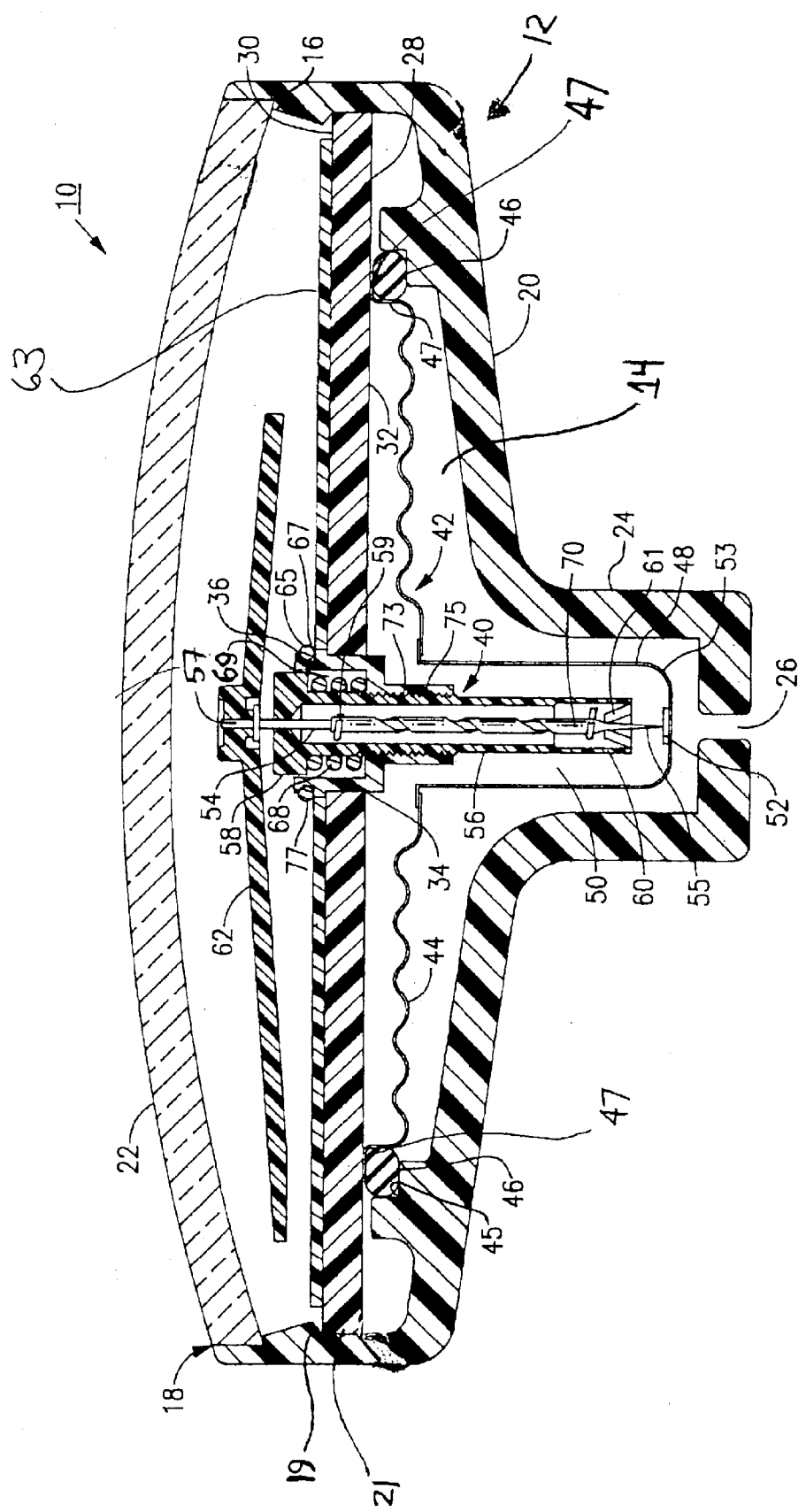
FIG. 1 is a side elevational view, shown in section, of a pressure measuring device according to the present invention.

Referring to FIG. 1, there is shown a blood pressure measuring device or apparatus 10 made in accordance with a first embodiment of the invention. The device 10 includes a substantially cylindrical gage housing 12 having an interior cavity 14 defined by a circumferential inner wall 16, an open top end 18, and a bottom end 20. A viewing window or bubble 22, made from glass, plastic, or other suitable transparent material is attached in a known manner to the open top end 18 of the gage housing 12. The bottom end 20 of the gage housing 12 has a diameter which inwardly tapers down to a narrow downwardly extending portion 24 having a bottom opening 26 serving as an inlet port for admitting a fluid. Preferably, the diameter of the narrow extending portion 24 is about one third of the diameter of the major portion of the housing 12, though it will be apparent from the following discussion that this parameter can be suitably varied depending upon the application.

The interior cavity 14 of the housing 12 is sized for retaining a number of component parts, including a horizontally disposed support plate 28. The support plate 28 is a generally planar member having opposing top and bottom facing sides 30, 32, and a central through opening 34. A press-fitted or otherwise suitably attached or integral sleeve 36 attached to the top facing side 30 of the support plate 28 extends into the central through opening 34 of the support plate 28 and is used for retaining a movement mechanism 40, described in greater detail below.

The circumferential inner wall 16 of the housing 12 further includes a reflexed portion 19 which is sized for supporting an outer edge 21 of the horizontal support plate 28 immediately there beneath and at a predetermined height within the housing 12. The central through opening 34 is shown as being substantially aligned with the bottom opening 26 of the housing 12, but this particular alignment is not critical to the workings of the present invention and therefore can be varied.

Figure 2:
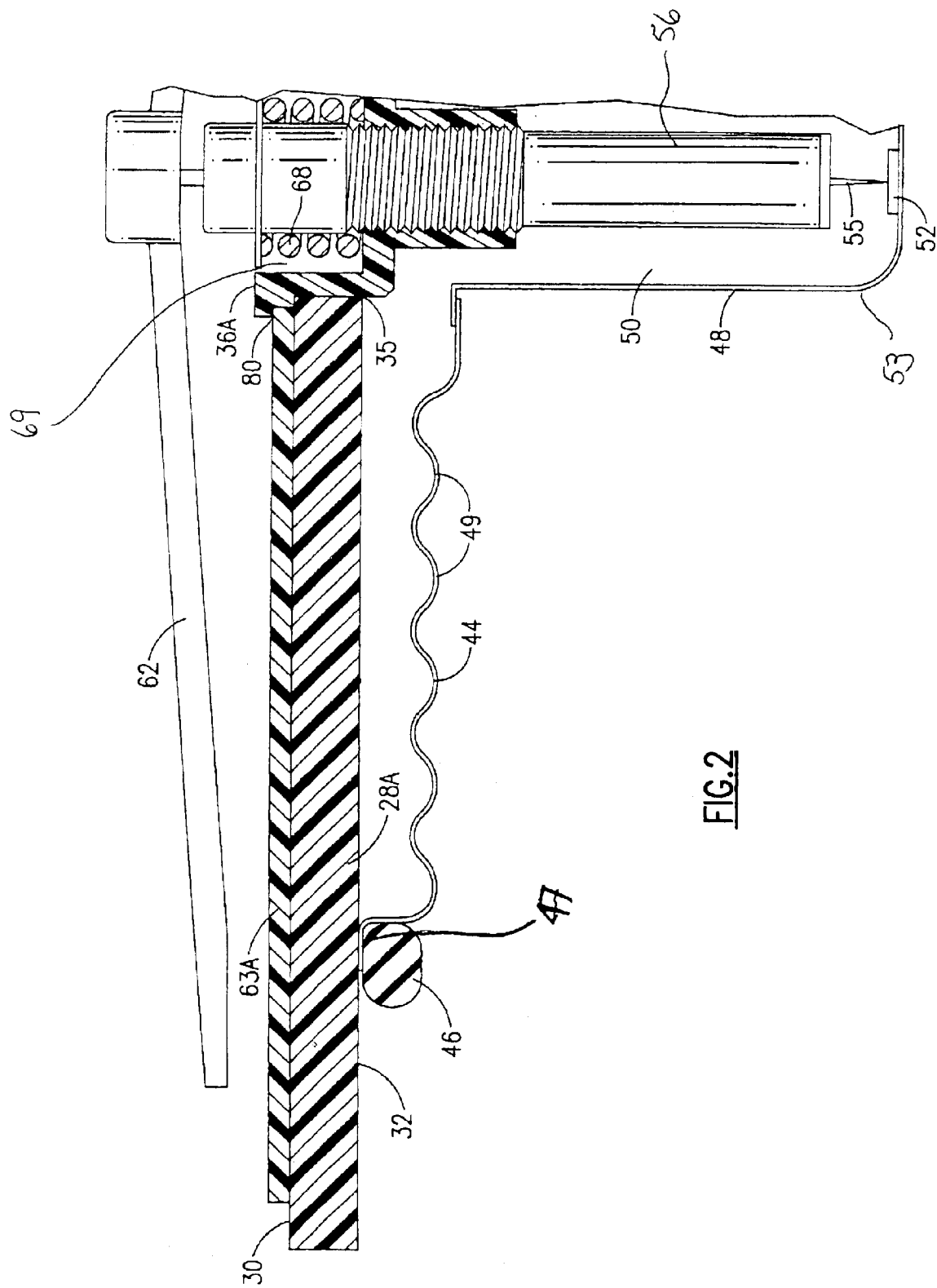
FIG. 2 is an enlarged sectional view of the pressure measuring device of FIG. 1, depicting alternate means for attaching a rotatable dial face in relation to the device.

Referring to FIGS. 1 and 2, a diaphragm subassembly 42 includes a flexible diaphragm 44 which is non-fixedly attached to the bottom facing side 32 of the horizontal support plate 28. The diaphragm 44 is substantially horizontally planar and includes a plurality of wave-like surfaces 49. An outer edge 47 of the diaphragm 44 is clamped by an O-ring 46 disposed on a circumferential ledge 45 extending upwardly from the bottom end 20 of the housing 12. The O-ring 46 not only supports the diaphragm 44 in place, but also provides a fluid tight sea for the bottom of the interior cavity 14.

The centermost portion of the horizontally planar diaphragm 44 includes a downwardly extending section, hereinafter referred to as the pan 48, which is soldered or otherwise fixed or even integral with the remainder of the diaphragm 44. The pan 48 is a hollow cylindrical section which extends into the downwardly extending portion 24 of the housing 12 when assembled and includes a cavity 50 having a width dimension that is substantially equal to that of the press-fitted sleeve 36. A lower end 53 of the pan 48 includes a interior contact surface 52 which is hardened.

Referring only to FIG. 1, the movement mechanism 40 includes an axially displace able shaft member 54 which is wholly enclosed within a tubular member 56 with the exception of protruding top and bottom ends 57, 55, respectively. A thin flexible ribbon-like spring member 70 is fixedly attached at one end 61 adjacent a bottom end of the tubular member 56 and at an opposite remaining end 59 to the axially displace able shaft member 54 around which the ribbon spring member 70 is helically or spirally wound. The outer tubular member 56 includes a set of external threads 73 extending over an upper portion of the length thereof which engage corresponding internal threads 75 provided in the press-fitted sleeve 36. The ribbon spring member 70 is preferably fabricated from beryllium copper, spring steel, or other similar material.

The hollow tubular member 56 includes an integral top cap portion 58 having a diameter which is larger than that of the remainder of the member, the cap portion having a shoulder which bears against a biasing spring 68 disposed within an annular recess 69 of the press-fitted sleeve 36. The top cap portion 58 and the biasing spring 68 are used to adjust the overall sensitivity of the movement mechanism 40.

When correctly positioned, the majority of the movement mechanism 40 extends beneath the horizontal support plate 28 and into the cavity 50 defined in the pan 48 which is already positioned in the downwardly extending portion 24 of the housing 12. In this position, the extending bottom end 55 of the shaft member 54 is proximate to the hardened contact surface 52.

Still referring to FIG. 1, a dial face 63 having measuring indicia (not shown) is attached to the top facing side 30 of the horizontal support plate 28 through a center opening which is sized to fit over the press-fitted sleeve 36. An O-ring 65 disposed in a slot 67 of the tubular sleeve 36 engages an inner edge of the dial face 63 with an indicating member 62 being mounted to the protruding top end 57 of the shaft member 54. A preferred lightweight indicating member useful in his design is described in U.S. Ser. No. 09/471,847, the entire contents of which are herein incorporated by reference.

In operation, changes in the pressure of incoming fluid (in this example, air) entering the bottom opening 26 of the housing 12 cause corresponding movements of the diaphragm 44. That is, the seal provided onto the outer edge 47 of the diaphragm 44 by the O-ring 46 clamping against the bottom facing side 32 of the horizontal support plate 28 prevents air from further penetrating into the interior cavity 14. Therefore, the increase in pressure causes axial movement of the diaphragm pan 48 with the interior contact surface 52 being caused to push upwardly against the bottom end 55 of the axially displace able shaft member 54. As a result of the upward movement of the diaphragm 44, the ribbon spring member 70 is caused to extend against the fixed end 61 of the tubular member 56, causing the shaft member 54 to rotate about its linear axis. The rotation of the axially displace able shaft member 54 therefore causes a corresponding circumferential movement of the indicating member 62 attached to the top end 57 of the shaft member 54 relative to the measuring indicia (not shown) on the dial face 63.

Zero adjustment of the above pressure measuring device 10 is a relatively simple procedure, as compared with previously known devices. First, the viewing window 22 is removed from the open top end 18 of the gage housing 12. The engagement of the O-ring 65 against the inner edge of the dial face 63 allows the dial face to be freely rotated in relation to the position of the indicating member 62. Sensitivity adjustments can also be made at the top of the device 10 by rotating the top cap portion 58 against the biasing spring 68 within the annular recess 69 of the press-fitted sleeve 36, so as to adjust the sensitivity of the ribbon spring member 70 for a given rotation. A similar mechanism is described in previously incorporated U.S. Pat. No. 6,168,566.

Variations of the above device are possible. For example and referring to FIG. 2 and in lieu of an O-ring, either the dial face 63A and/or the horizontal support plate 28A can be tapered suitably adjacent their center openings relative to a slot 80 provided in the tubular sleeve 36A in order to allow the dial face to be rotated without requiring removal. Alternately, the movement mechanism 40 can include a zero adjustment feature as described in U.S. Pat. No. 5,966,829 and U.S. Pat. No. 6,168,566. In passing, it should be noted that FIG. 2 merely illustrates a portion of the overall assembly in order to distinctly facilitate the above discussion.

Figure 3:
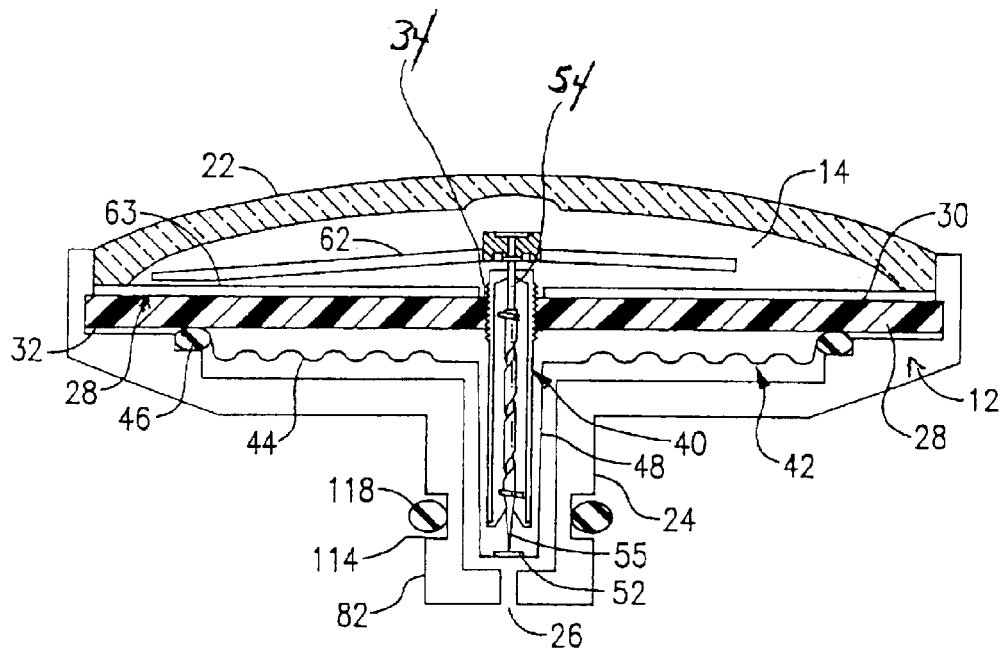
FIG. 3 is a side elevational view, shown partly in section, of a pressure measuring device having a housing according to a second preferred embodiment.

A housing design in accordance with a second embodiment is illustrated in FIG. 3. Similar parts are herein labeled with the same reference numerals for the sake of clarity. As in the preceding, the device includes a gage housing 12 having an interior cavity 14 sized for retaining a diaphragm assembly 42 which includes a diaphragm 44 having a series of wave-like surfaces 49 as well as a downwardly extending portion or pan 48. The device further includes a substantially horizontally disposed planar support plate 28, the housing 12 further having a downwardly extending narrowed portion 24. A movement mechanism 40 is disposed through a central opening 34 defined in the horizontal support plate 28 such that the bottom end 55 of an axially displace able shaft 54 of the mechanism is disposed in proximity to a hardened contact surface 52 of the pan 48 of the diaphragm assembly 42. The diaphragm 44 in the meantime is attached, but sealed, to the bottom facing side 32 of the horizontal support plate 28.

Fluid, such as air, entering the gage housing 12 through a bottom opening 26 causes deflection of the pan 48 of the diaphragm 44 against the axially displace able shaft 54, thereby causing rotation of the shaft by means of an attached ribbon spring member 70, according to the manner previously described.

According to this particular embodiment, the device includes a docking hub 82 provided on the exterior of narrow downwardly extending portion 24 of the housing 12, the hub including a circumferential slot 114 which is sized for retaining an O-ring 118 or other similar sealing element. For example, the docking hub 82 can utilize pipe or other form of known threads (not shown). The docking hub 82 provides adequate modification to allow the device to be attached to other existing pressure device housings having pressure sources, for example, those manufactured by Welch Allyn, Inc. of Skaneateles Falls, N.Y., among others. In passing, it should be noted that the position of the bottom opening 26 of the housing 12 is not essential; that is, incoming fluid can enter the housing 12 from either a horizontally or otherwise disposed port, so long as the opening is beneath the seal which is provided by the O-ring 118.

Figure 4:
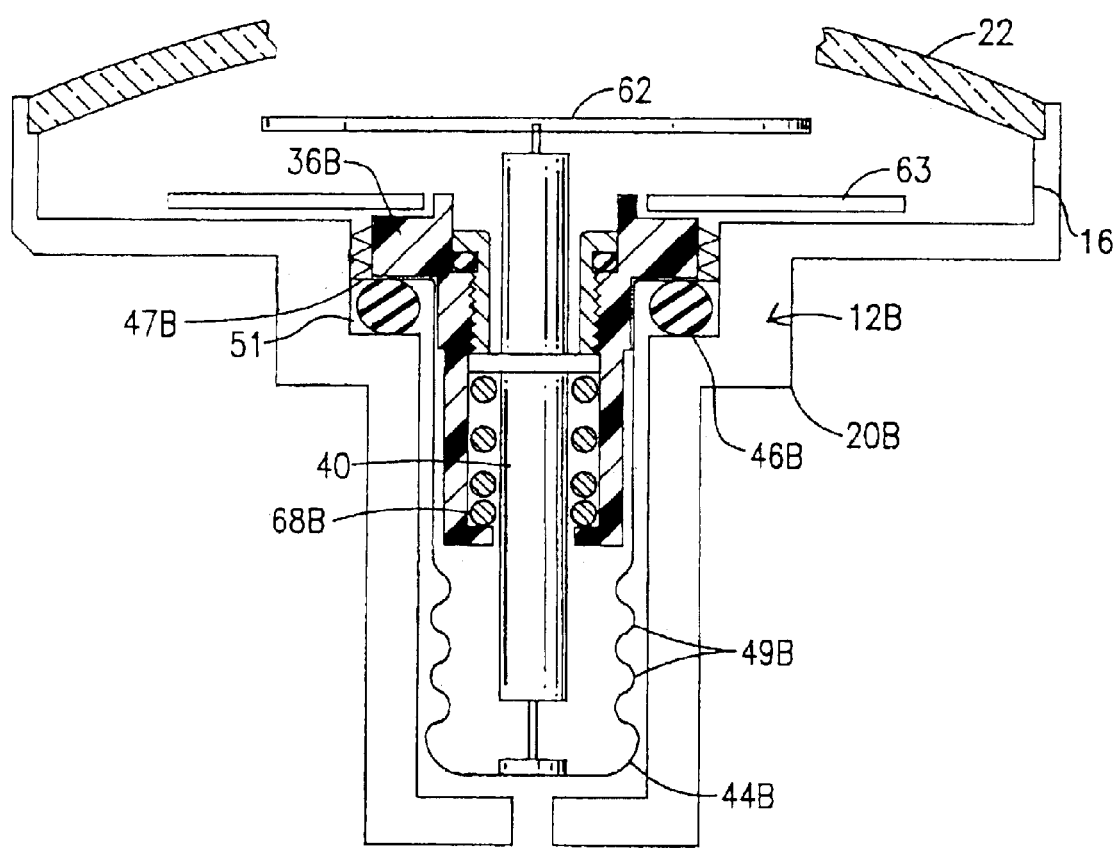
FIG. 4 is a side elevational view, shown partly in section, of a pressure measuring device having a housing according to a third preferred embodiment.

To further illustrate variations and referring to FIG. 4, a third embodiment of a housing 12B made in accordance with the present invention includes a diaphragm 44B, which unlike the preceding embodiments, is a substantially vertical member having an overall width dimension that is considerably narrower than those previously described. As a result, a horizontal support plate is not required as in the preceding which is fitted to the circumferential inner wall 16 of the housing 12B.

Like the preceding embodiments, an outer edge 47B of the diaphragm 44B is sealed using an O-ring 46B or other sealing member which effectively clamps the outer edge to a shoulder of the a press-fitted sleeve 36B. The movement mechanism 40 is disposed essentially through a center opening in a press-fitted sleeve 36B and threaded into engagement therewith. The majority of the movement mechanism 40 is disposed within the cavity defined by the essentially vertical diaphragm 44B, the particular diaphragm of this embodiment having vertically disposed wave-like surfaces 49B. Adjustments to control the sensitivity of the movement mechanism 40 using biasing spring 68B are performed in the manner previously described.

Overall, the housing of the instant embodiment defines a very shallow profile for the upper portion of the gage housing 12B. Though not shown, the bottom end 20B of the gage housing 12B can be used as a docking hub to secure the gage housing into other gage housings (not shown) either as a retrofitted or as a new assembly as previously described. As further described herein, this docking hub can also permit direct hose-free connection between a gage housing and an inflatable blood pressure sleeve.

Figure 5:
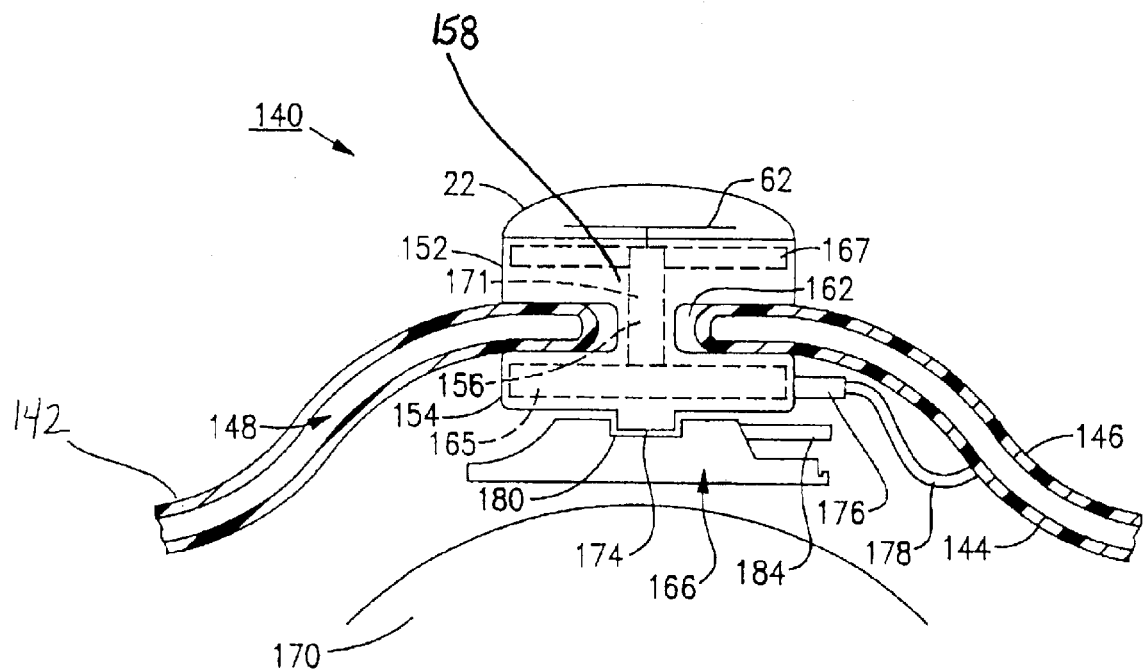
FIG. 5 is a partial sectional view of a pressure measuring device made in accordance with a fourth preferred embodiment as used with an inflatable blood pressure sleeve.

Referring to FIG. 5, a gage or instrument housing 140 formed in accordance with a fourth embodiment of the present invention is herein described in combination with a blood pressure sleeve or cuff 142. For purposes of the present embodiment, the instrument housing 140 is used with a specific blood pressure cuff which is described in greater detail in U.S. Pat. No. 6,036,718, the contents of which are hereby incorporated in its entirety. In brief, the inflatable cuff 142 is manufactured using a pair of sleeve portions 144, 146 which are sealed together using a series of continuous RF (radio frequency) welds to form an integral bladder less structure having an inflatable inner volume 148.

In operation, the cuff 142 is then wrapped as conventionally known about the arm 170 (partially shown) or other limb of a patient.

The gage housing 140 includes an upper housing portion 152, a lower housing portion 154, and a connecting intermediate portion 156. The upper and lower housing portions 152, 154 are substantially cylindrical in cross section and have approximately the same dimensions while the intermediate portion 156 has a substantially smaller diameter that is considerably narrower than either adjoining section, thereby defining a configuration resembling a yo-yo. According to the present embodiment, the intermediate portion 156 has a diameter which is approximately one third the diameter of the remaining portions 152, 154, but it will be readily apparent that this parameter can be varied depending on the relative size of the movement mechanism used therein. Each of the above portions 152, 154, 156 are interconnected and hollow, combining to form an interior cavity 158.

According to this embodiment, a horizontal support plate 165 (shown in phantom) is positioned within the lower portion 154 of the housing 140 while a dial face 167 (also shown in phantom) is disposed in the upper portion 152. A movement mechanism 171 (also shown in phantom) which is similar structurally to those previously described, interconnects the dial face 167 and the support plate 165 and is located primarily in the intermediate portion 156.

According to this embodiment, a slot 162 is cut into one of the sleeve portions 144, 146. The slot 162 provides a button-like retainment for the lower portion 154 of the housing 140 as well as the intermediate portion 156, with the upper portion 152 protruding from the exterior of the cuff 142. A port 176 is connected via a hose 178 to the inflatable inner volume 148 of the cuff 142 which is inflated by a pneumatic bulb (not shown) in a well known manner.

In operation, the device operates similarly to that previously described, except that a detachable stethoscope adapter 166 can also be attached to the bottom of the lower housing portion 154, thereby forming an integral unit. The bottom of the lower portion 154, according to this embodiment, includes an extending attachment portion 174 sized to engage a female connector 180 or other suitable means provided on the adapter 166. All preceding known cuffs require separation between the cuff and the stethoscope. With the overall shallow profile of the above housing 140, use of an adapter 166 permits an interconnection which is highly advantageous.

The stethoscope adapter 166 is a conical member which forms the bell of the stethoscope having connecting ear pieces (not shown) attached to a port 184. In use, the adapter 166 is freely rotatable relative to the housing 140, allowing examination by a patient or care giver to be performed equally well. The overall workings of stethoscopes are commonly known and do not form part of the inventive concepts described hereon.

Figure 6:
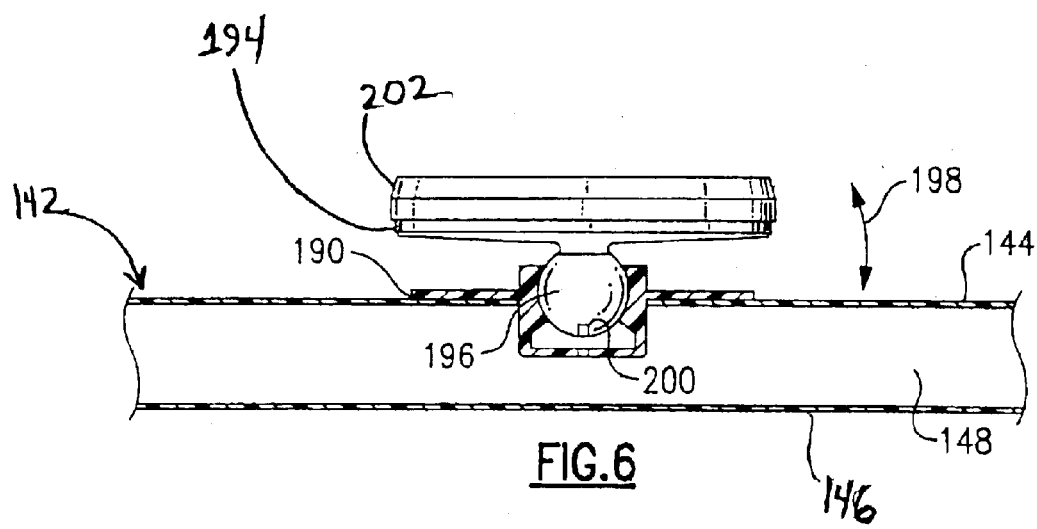
FIG. 6 is a side elevational view, partly in section, of a pressure measuring device made in accordance with a fifth preferred embodiment of the present invention.
Figure 7:
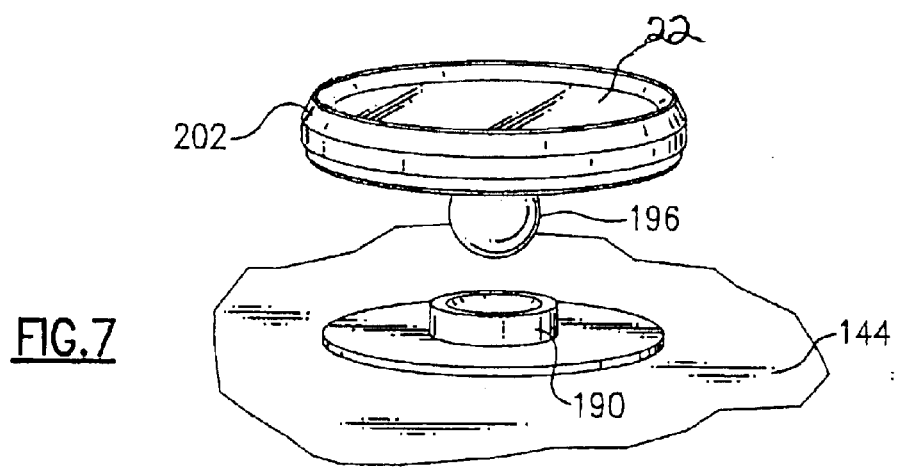
FIG. 7 is an unassembled view of the pressure measuring device of FIG. 6.
Figure 8:
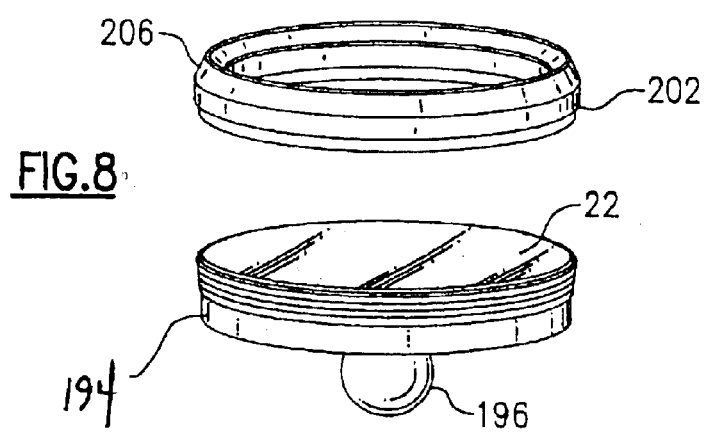
FIG. 8 is a partially exploded view of the housing of the pressure measuring device of FIGS. 6 and 7.

Referring to FIGS. 6–8, there is shown a blood pressure measuring device made in accordance with a fifth embodiment of the present invention. As in the preceding, similar parts are labeled with the same reference numerals for the sake of clarity. This device includes an RF welded blood pressure sleeve 142 similar to that described in the previously incorporated '718 patent including a pair of sleeve portions 144, 146 which are sealed together to form an integral structure and define an inflatable inner volume 148. The sleeve 142 is sized to be wrapped around the arm or other limb of a patient (not shown) in a manner which is commonly known, and therefore requiring no further explanation. A socket 190 is disposed and fixed within a slot which is provided on the exterior of one of the sleeve portions 144, the socket being sized to receive a mating portion of an instrument or gage housing 194. The instrument housing 194 according to this embodiment is similar to those previously described including a narrowed bottom portion, but in which the bottom portion also includes a ball-shaped engagement or mating end 196. When assembled, the ball-shaped engagement end 196 is fitted within the socket 190 of the sleeve in order to provide a direct fluid and sealed connection therewith, the gage housing 194 being free to pivot about the plane of the sleeve 142 as shown by reference numeral 198.

The engagement end 196 includes an opening 200 which permits fluid communication with the interior of the sleeve 142 wherein fluid (air) can enter the interior of the gage housing 194 to cause corresponding movement of a diaphragm and a contained movement mechanism (not shown), in the manner previously described herein.

Preferably, the viewing window 22 of the housing 194 includes an anti-reflective coating to reduce or substantially reduce glare, with the user (physician or care giver) or patient having the ability to either rotate the housing or to pivot same in order to effectively utilize the instrument and read the dial face. As such, the gage housing 194 can effectively be used in either a right or left armed patient measurement. A sleeve which further provides this ability with an attached gage housing is described in greater detail below.

Still referring to FIGS. 6–8, the device further includes a rubberized ring-shaped guard or bumper 202 which is press-fitted into engagement about the outer periphery of the gage housing 194, the bumper having a ridge 206 which extends a predetermined distance above the viewing window 22. The bumper 202 performs at least two functions; first, and though the present device is ultra lightweight, the bumper additionally absorbs shock or impact loads when the housing 194 is dropped. Second, the bumper 202 also prevents damage to the viewing window 22.

As described in greater detail in a succeeding embodiment, it should be noted herein that the mating or engagement end of the narrowed bottom portion of the instrument or gage housing need not include a ball-shape for accommodation within the sleeve socket 190. Examples are discussed below with reference to FIGS. 9–14.

Furthermore, it should also be apparent that other conventionally known gage housings which include a pressure responsive member can be configured or retrofitted for direct engagement with a blood pressure sleeve without requiring hoses (hoseless) between the housing and the sleeve. An example is partially shown in FIG. 15, a gage housing 296 retaining a conventional movement mechanism 292. The movement mechanism 292 includes a threaded end 297 which extends through a bottom opening 299 of the housing 296 and is received into the mating threaded end of a port 300 of a tubular member 305, the input end of which includes a pneumatic bulb 307. In use, the output end 309 of the tubular member 305 receives a hose (not shown) which extends to a coupling of a blood pressure sleeve (not shown).

Figure 15:
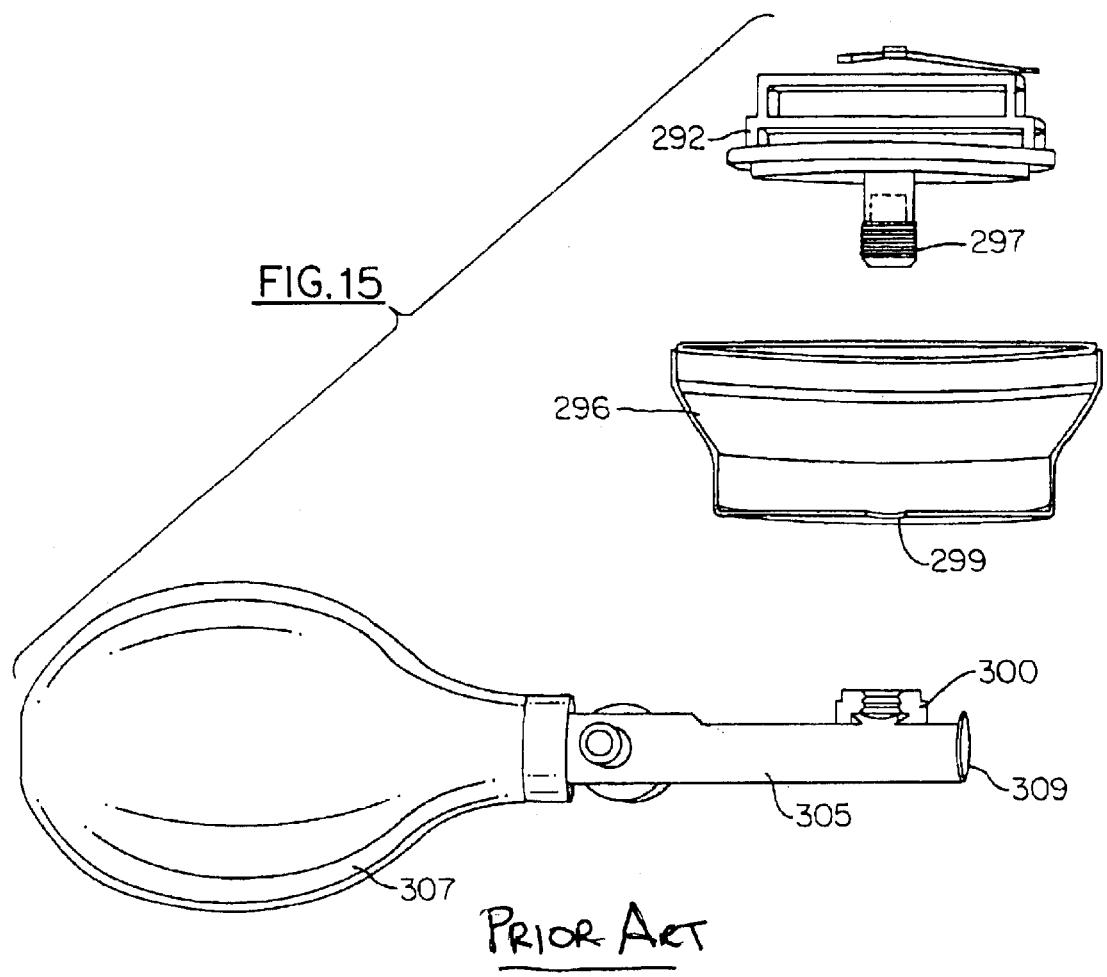
FIG. 15 is a partially exploded view of a conventional blood pressure measuring apparatus.
Figure 16:
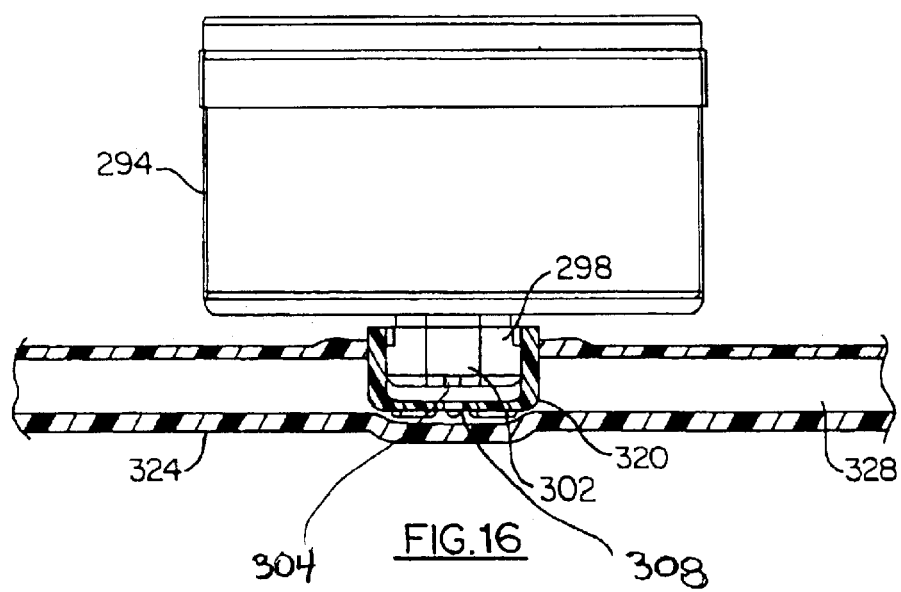
FIGS. 16 and 17 are side elevation views, partly in section, of conventional gage housings which have been configured for direct attachment to an inflatable blood pressure sleeve.
Figure 17:
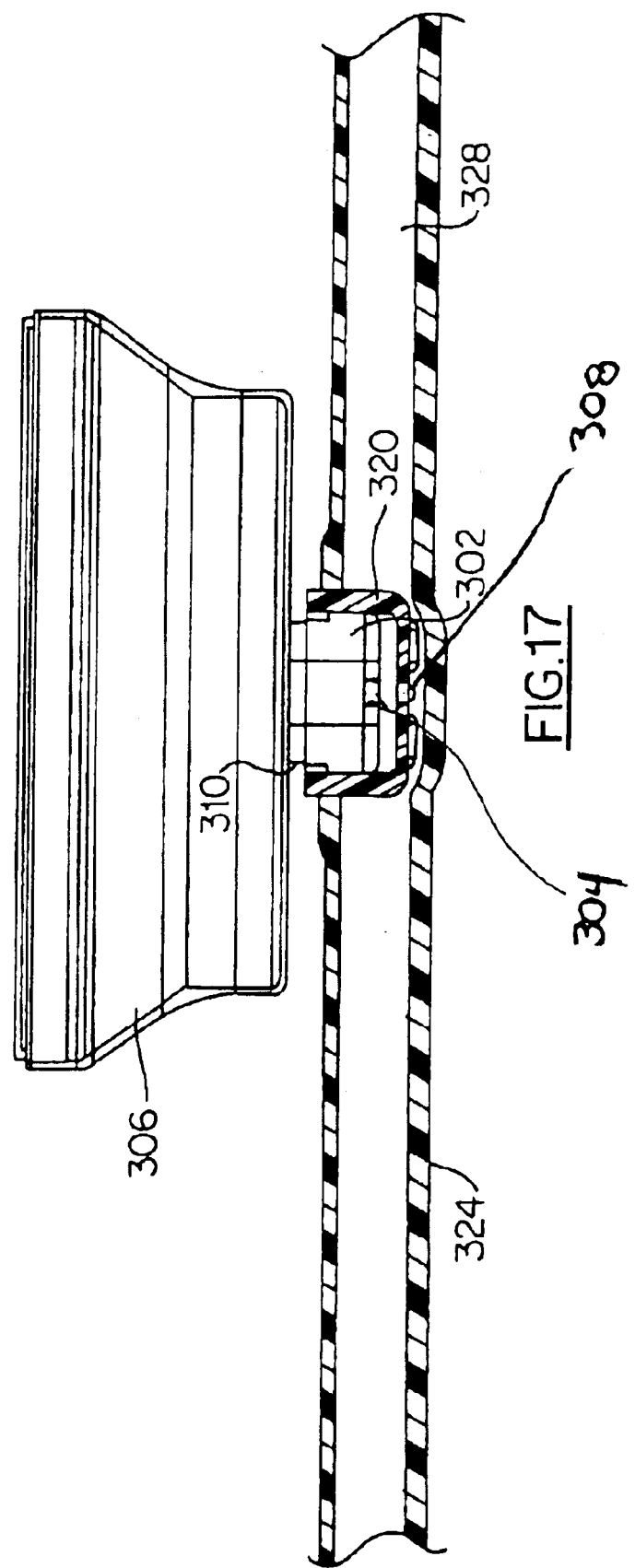

Referring to FIGS. 16 and 17, respectively, a pair of known gage housings 294, 306 are shown which can be interconnected to a blood pressure sleeve 324 in a manner similar that previously described. Each of these conventional housings 294, 306, similar to those of FIG. 15, are less compact than those which have been expressly detailed, mainly because of the intricacy and sizing of the movement mechanism that is contained therein. Each of the gage housings 294, 306, however, do commonly contain a threaded engagement end or inlet port 298, 310, which permits fluid communication between the housing interior and the pneumatic bulb 307, FIG. 15. The bulb 307 is attached using a hose (not shown) to the inlet port. Literally any gage housing having an engagement or inlet end and including literally any form of movement mechanism can be reconfigured according to the present invention for hoseless interconnection with an inflatable sleeve.

According to the present invention and in order to retrofit the gage housings 294, 306, the end of the threaded inlet port 298, 310 can be covered with an adapter or cap 302 which is sized for sealing engagement within a socket 320 provided in an inflatable blood pressure sleeve 324. The cap 302 and the socket 320 each include respective openings 304, 308, which as shown in FIGS. 16 and 17 upon attachment to the inflatable sleeve 324, permits direct fluid communication between the interior 328 of the sleeve 324 and the interior of the housing 294, 306, the housing being preferably snap-fitted to the sleeve. As a result, there is no need to include the tubes which are essential to the prior art assembly of FIG. 15, thereby greatly simplifying the use of even conventional devices by permitting direct, hose free connection to an inflatable blood pressure sleeve.

In passing, it should further be noted that though an RF welded or bonded inflatable sleeve is described throughout, other forms of inflatable sleeves can be utilized embodying the central concepts of the present invention, including both bladderless sleeves and sleeves having bladders. Furthermore, and though the above concept relies upon a releasable snap-fit coupling between a socket and mating engagement end of a gage housing, there are other coupling schemes such as interference fits, fitted slots and the like, as well as integral fits between a sleeve and gage housing which are intended to be covered as part of the inventive aspects of the present invention.

Figure 9:
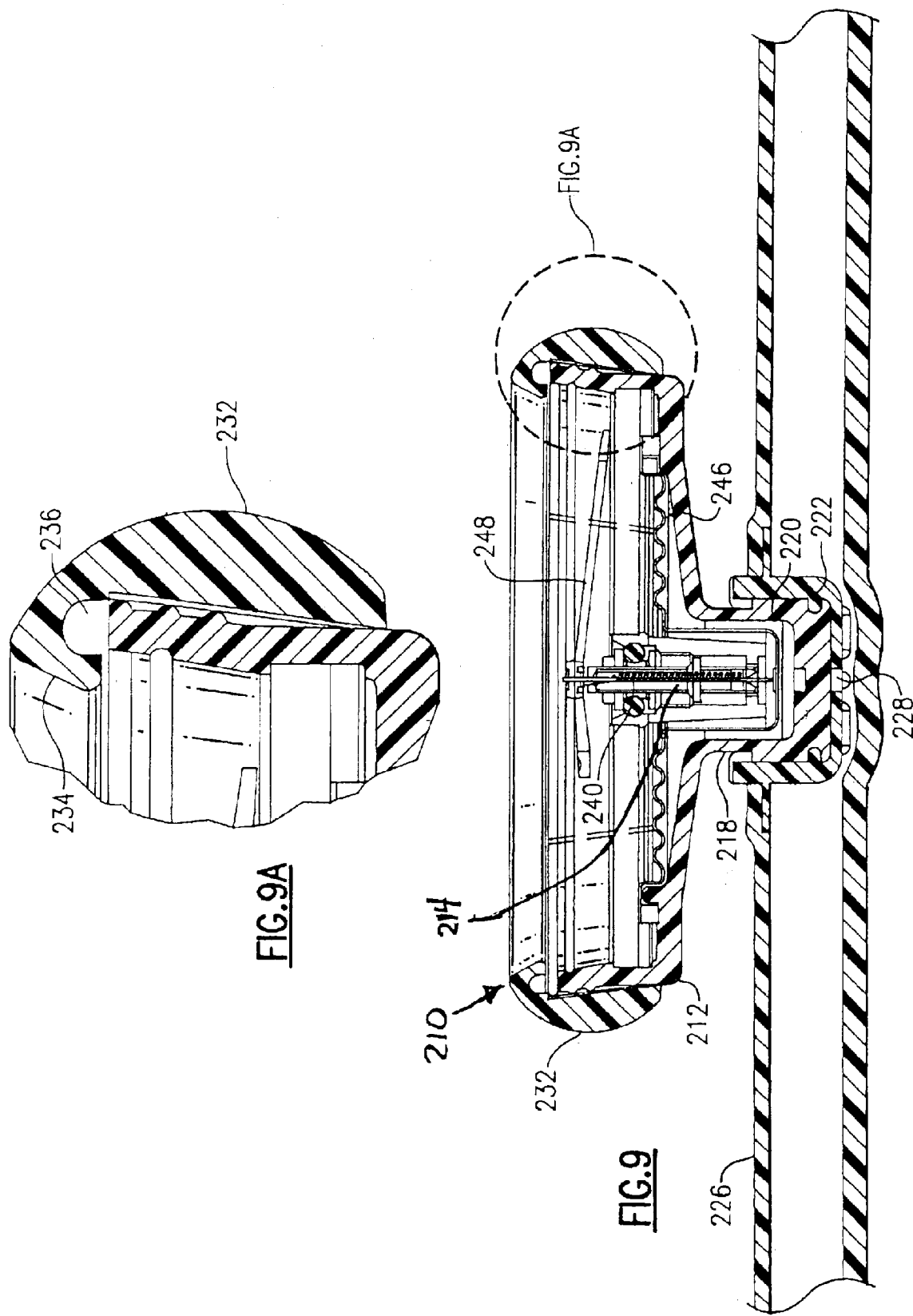
FIG. 9 is a side elevational view, in section, of a gage housing made in accordance with a sixth embodiment of the present invention.
Figure 10:
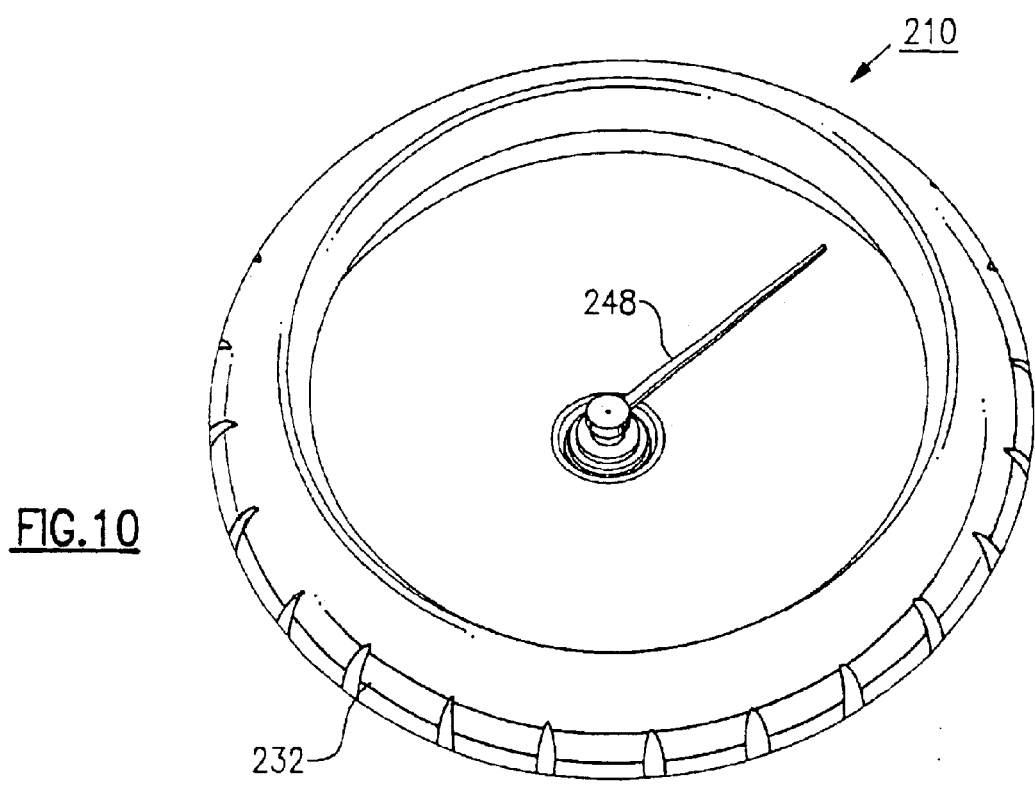
FIG. 10 is a top perspective view of the gage housing of FIG. 9.
Figure 11:
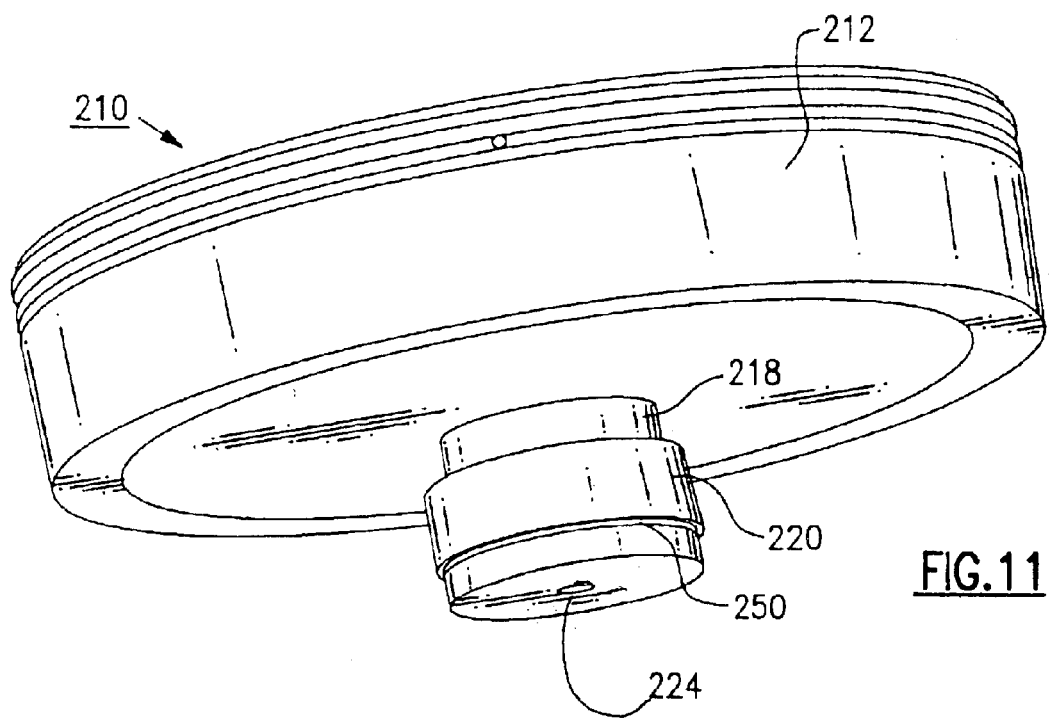
FIG. 11 is a side perspective view of a gage housing made in accordance with a seventh embodiment of the present invention.
Figure 12:
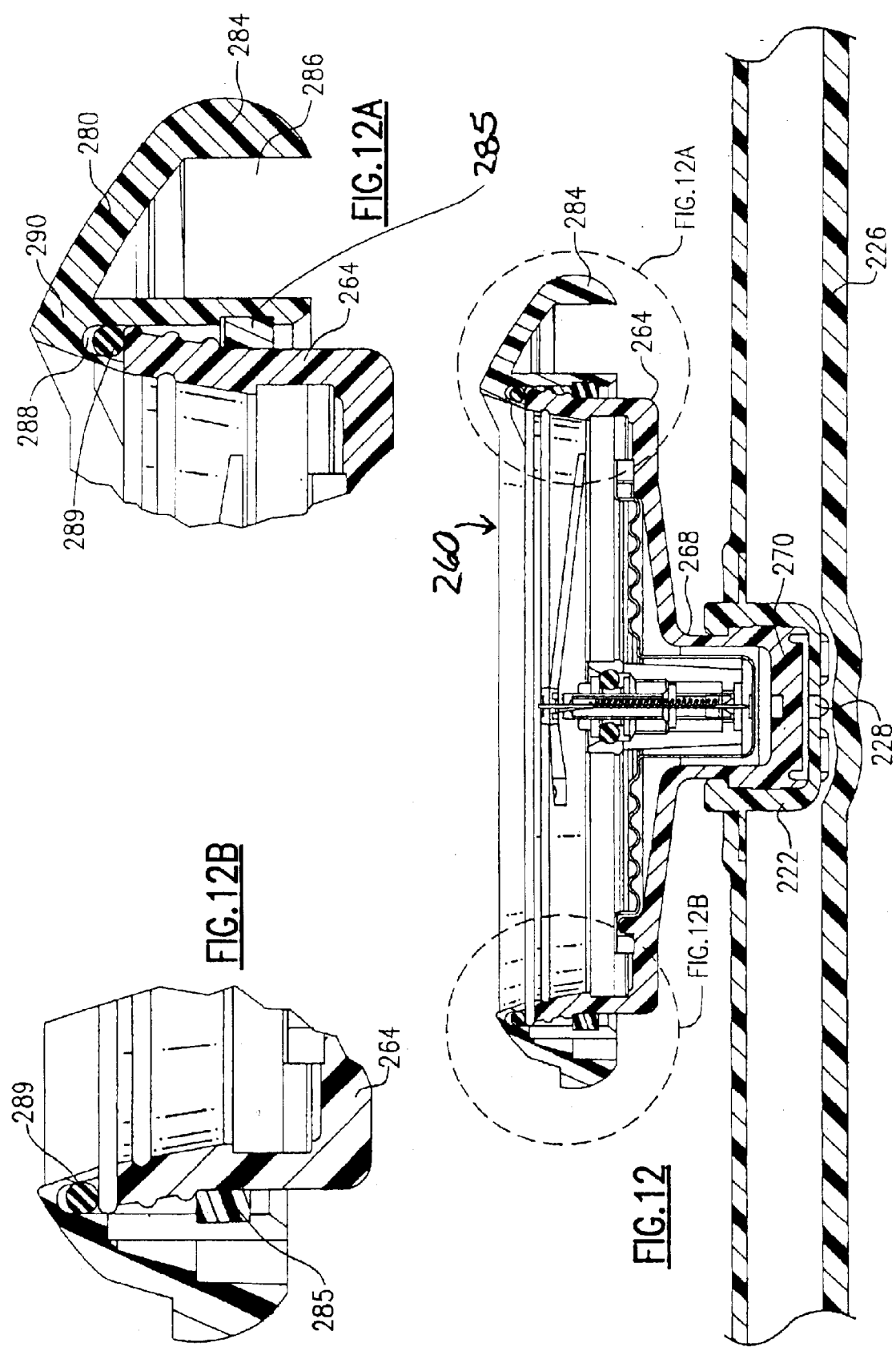
FIG. 12 is a side elevational view, in section, of the gage housing of FIG. 11.
Figure 13:
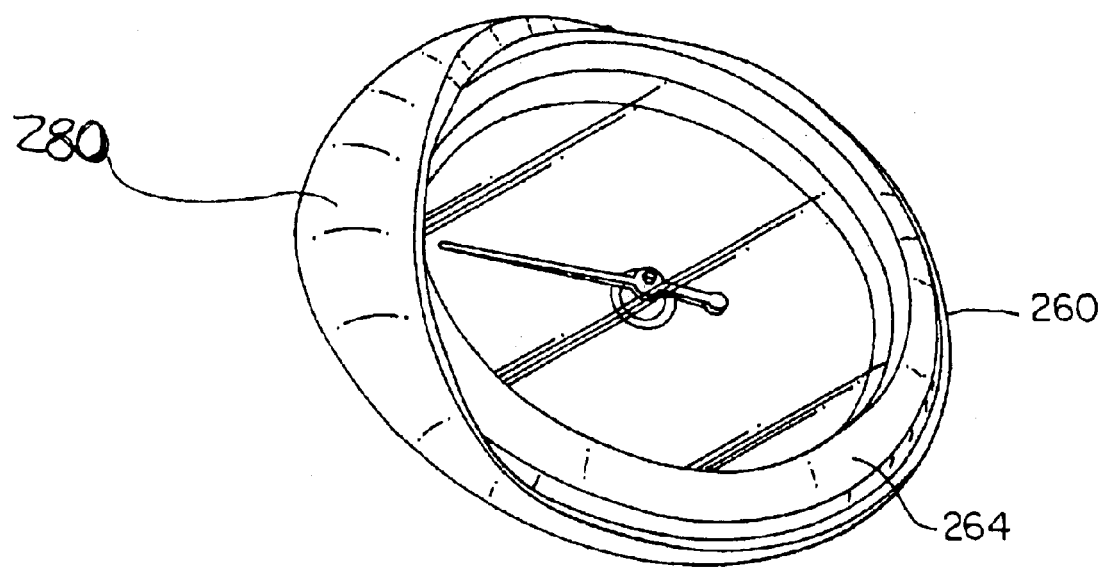
FIG. 13 is a top perspective view of the gage housing of FIG. 12.
Figure 14:
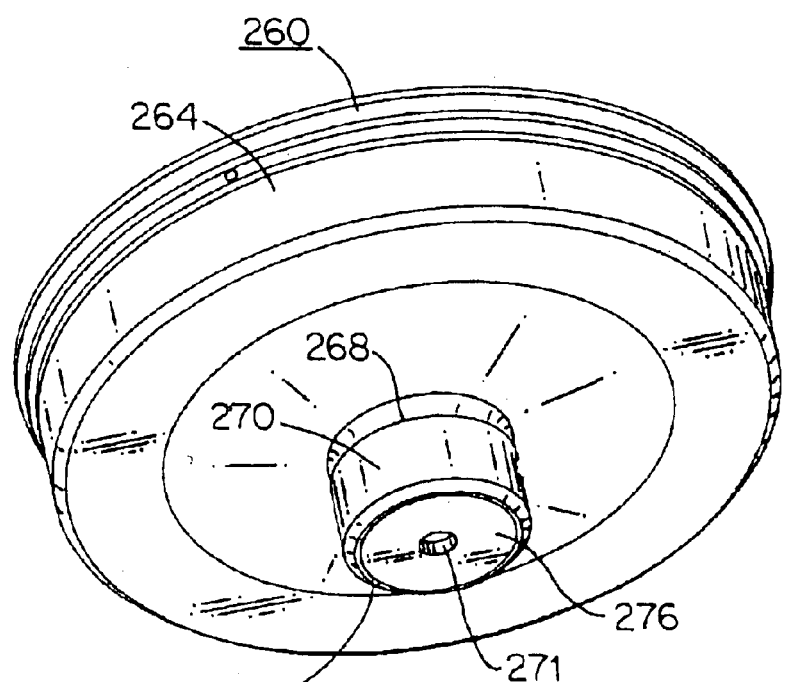
FIG. 14 is a bottom perspective view of the gage housing of FIG. 12 having a shock resistant feature made in accordance with another embodiment of the present invention.

Referring to FIGS. 9–11, there is shown a gage or instrument housing 210 according to a sixth embodiment of the present invention. As in the preceding, the gage housing 210 is used in connection with a blood pressure measuring device and includes an upper housing portion 212 which retains a movement mechanism 214 and a narrowed lower portion 218 having a mating or engagement end 220 which is sized to engage a generally cylindrical socket 222 formed in a sleeve portion of a bladderless blood pressure cuff or sleeve 226. Unlike the preceding embodiment, the mating end 220 of the narrowed lower portion 218 is also generally cylindrical in cross section, the end similarly including an end opening 224, shown in FIG. 11, which permits fluid communication with the interior of the blood pressure cuff 226 via a corresponding opening 228 also formed in the socket 222, thereby forming a fluid inlet port.

The upper housing portion 212 of the gage housing 210 and the contained movement mechanism 214 are similar to those previously described. That is, the movement mechanism 214 includes a helically wound thin ribbon spring 240 which is attached at one end to an axially displaceable shaft member and at a second end to a tubular sleeve member in the manner described above. Changes in pressure of the cuff 226 cause fluid to enter the narrowed lower housing portion 218 through the end opening 224, affecting a contained diaphragm 246 and causing the axially displaceable shaft member to be translated upwardly, resulting in rotation of the shaft member against the biasing of the ribbon spring 240 and circumferential movement of an indicating member 248, attached to a protruding top end of the shaft member, relative to a dial face.

The mating end 220 of the narrowed lower housing portion 218 further includes a circumferential channel or notch 250, which is most clearly shown in FIG. 11. The circumferential channel 250 provides a discontinuous path for shock and impact loads and, therefore, effectively cushions the contents of the gage housing 210 including the movement mechanism 214, from shock or impact loads such as when the housing 210 lands on the narrowed lower portion 218.

According to this embodiment and as most clearly shown in FIGS. 9 and 10, and to further insulate the housing 210 from damage due to shock or impact loading, a rubberized peripheral guard or bumper member 232, sized to fit over the exterior periphery of the upper housing portion 212 is press fitted into engagement therewith. The guard member 232 is similar to that previously described above in that the entire periphery of the upper housing portion 212 is covered, the guard member including a stepped portion 234, shown in FIG. 9A, which extends over the top of the upper housing portion, including the viewing window, and defines an air gap 236 along the outer circumferential edge thereof. The air gap 236 provides a discontinuous path for any impact loads which can occur if the gage housing 210 lands awkwardly.

Variations of the above embodiment of FIGS. 9–11 are possible. For example, and referring to FIGS. 12–14, there is shown a gage housing 260 according to a seventh embodiment of the present invention. The gage housing 260 also includes an upper housing portion 264 and a narrowed lower housing portion 268 having an engagement end 270 which mates with a socket 222 which is formed in blood pressure sleeve 226. The upper housing portion 264 according to this embodiment is defined by a substantially elliptical cylindrical cross section as opposed to the preceding embodiments in which the upper housing portions are substantially circular cylinders. It should be noted that other shapes or geometries could be contemplated. According to this embodiment, a circumferential channel 272 provided in the bottom surface 276 of the engagement end 270 provides a similar function to the axial circumferential channel 250, FIG. 11, with regard to shock or impact loads applied to the housing if dropped or otherwise acted upon.

Otherwise, the engagement end 270 similarly engages the socket 222 of the sleeve 226, the gage housing 260 retaining a movement mechanism (not shown) as previously described. The engagement end 270 includes an end opening 271 which permits hoseless fluid communication with the sleeve 226, also as previously described, through a socket opening 228 which extends to the sleeve interior.

According to the instant embodiment, a rubberized guard member 280 is press fitted over the exterior periphery of the upper housing portion 264, the guard member according to this embodiment including a radially extending portion 284 which when attached extends from the outer edge of the elliptically shaped upper housing portion 264 and similarly provides a cushioning air gap 286 which creates a discontinuity, in fact a buffer, which insulates the housing 260 from impact loads when the housing is dropped. Similar air gaps 288 are provided above the viewing window as defined in an axially extending portion 290 to provide additional protection against shock or impact loads.

As shown in FIG. 12A, an O-ring 289 is provided within the annular air gap 288. Additional shock resistance between adjoining portions of the housing 264 and the interior wall surface of the guard member include an annular rubberized shim 285.

Figure 18:
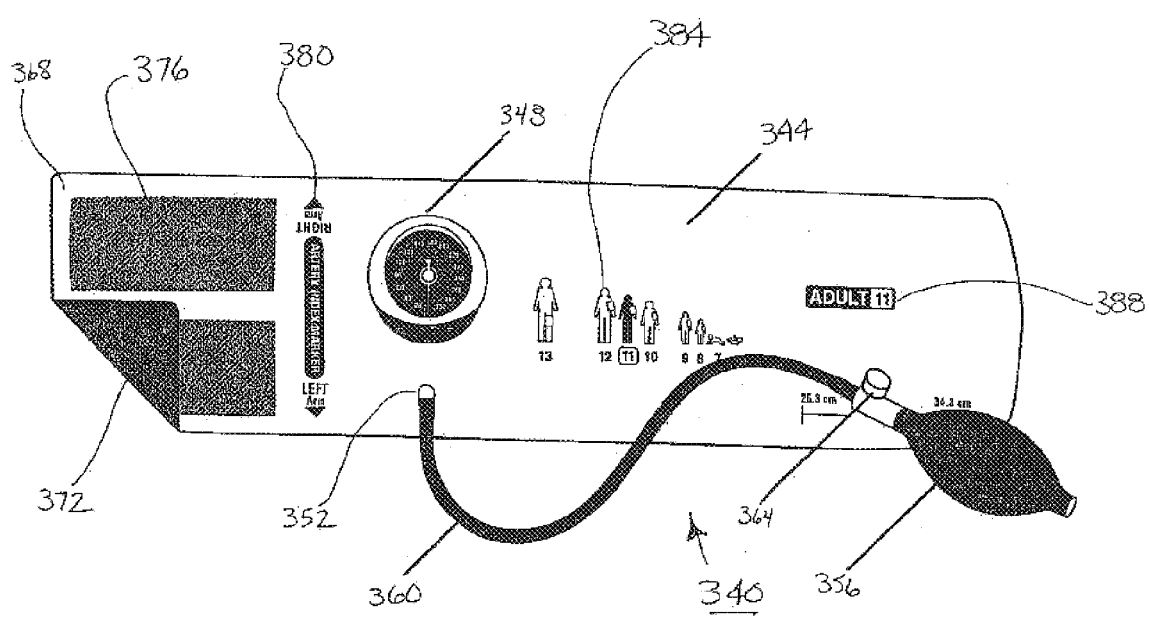
FIG. 18 is a top view of a blood pressure measuring apparatus in accordance with a preferred embodiment of the invention.
Figure 19:
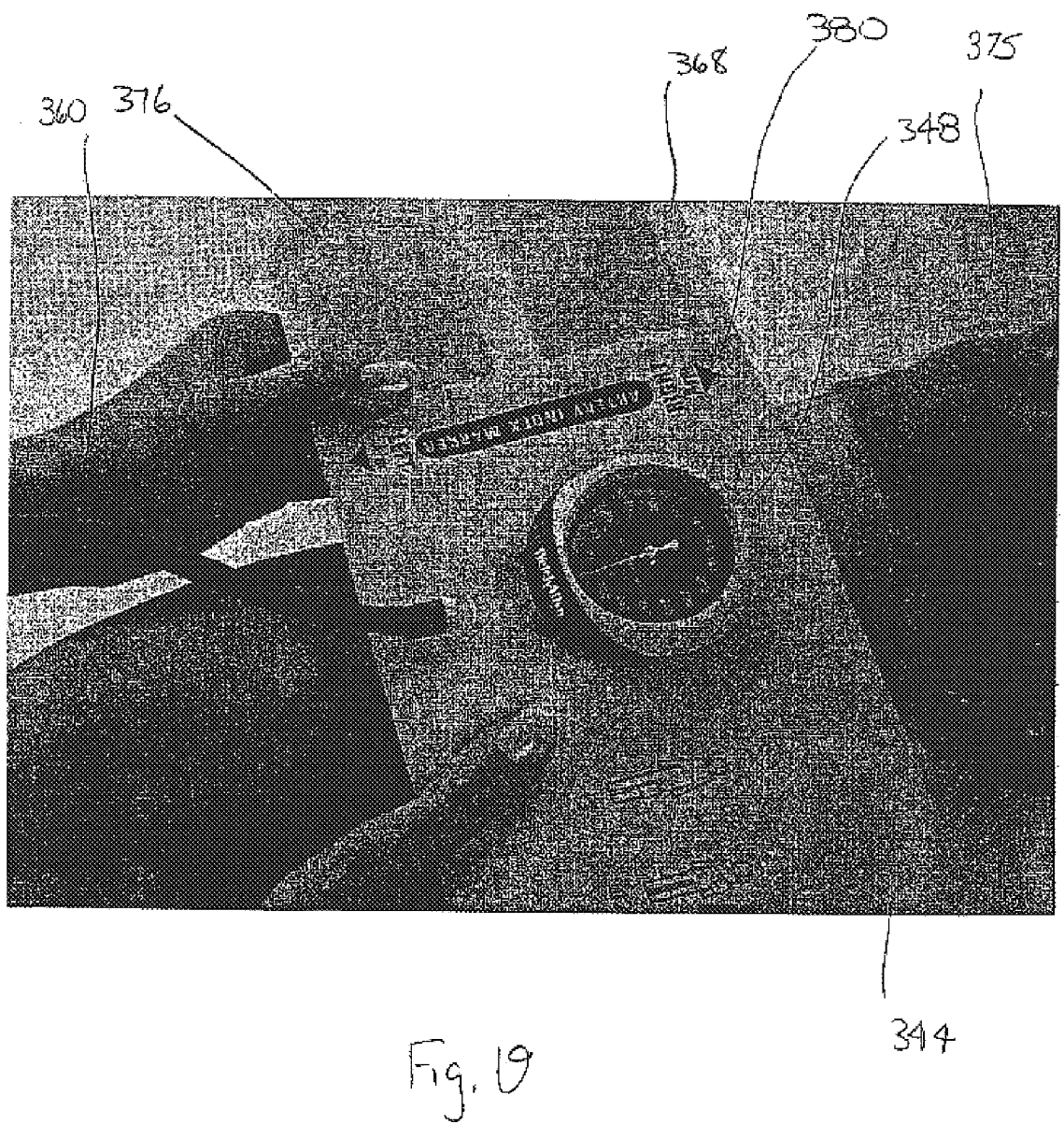
FIG. 19 is a perspective view of the inflatable sleeve of the apparatus of FIG. 18 as used with a patient.

Referring to FIGS. 18 and 19, a sleeve 344 for a blood pressure measuring apparatus 340 is herein described.

The sleeve 344 itself is constructed from a pair of sleeve portions 368, 372 made from a polyamide or other similar fluid impermeable material which are RF welded or bonded together and define an interior chamber. The interior chamber of the sleeve 344 is inflated by means of a pneumatic bulb 356 which is tethered by tubing 360 to a barb or port 352 provided on a sleeve portion 368, the barb having an opening which is in communication with the interior chamber of the sleeve. A check valve 364 provided adjacent to the pneumatic bulb 356 permits depression thereof when the valve is opened.

The sleeve 344 includes hook and loop fastener portions (only one of which 376 being shown) on the outward facing sides of each of the sleeve portions 368, 372 at opposite ends of the sleeve, thereby permitting the sleeve to be formed into a cylindrical shape and secured when wrapped about the limb of a patient 375, as shown in FIG. 19. Each hook and loop fastener portion 376 is also preferably RF welded to a sleeve portion 368, 372. Specific features relating to the above noted features, including the manufacture of the herein described sleeve 344, are described in U.S. Pat. No. 6,036,718, herein previously incorporated by reference in its entirety.

When properly attached, the facing side of the sleeve portion 372 contacts the patient with the facing side of the sleeve portion 368 being exposed. According to the present embodiment, each facing side has a different color to assist in attaching same to the patient. According to the present embodiment, the sleeve 344 is two-toned with the facing side of the sleeve portion 372 having a black colored finish and the facing side of the exposed sleeve portion 368 having a lighter colored finish.

A socket or port (not shown) similar to those described above and shown for example in FIGS. 9 and 12 is also provided in the sleeve portion 368, the socket being sized for receiving a gage housing 348 which is releasably snap-fitted in the manner previously described and defined. The gage housing 348, when attached, can be rotated about its vertical axis, permitting easy visual access to either the care giver and/or the patient.

The gage housing 348 according to this embodiment is identical to that previously shown and described in FIG. 9, the housing containing a bellows assembly as well as a gearless movement mechanism which operates in the manner described above to permit circumferential movement of an indicating member relative to a dial face when pressure changes within the interior chamber of the sleeve 344 cause movement to a movable surface of the bellows assembly. The gage housing 348 also preferably includes the shock/impact resistant features previously described.

An artery index marker 380 is provided adjacent the hook and loop fastener portion 376 on the facing side of the sleeve portion 368. This marker 380 is used to align the sleeve with the brachial artery of the patient, the marker further including left and right limb indicators which are provided on respective lateral sides of the sleeve 344. When the sleeve 344 is wrapped over the arm of the patient 375, the marker is used to properly and circumferentially align the arm and the artery with the limb indicator pointing directly at the artery. The rotatability of the gage housing 348 within the sleeve 344 permits the sleeve having the attached gage housing to be used when attached regardless of orientation.

According to the present invention, sets of indicia 384, 388 are also provided on the facing side of the sleeve portion

368 designating the size of sleeve being used; that is, whether the sleeve is an adult, child or neonatal cuff. An adult sleeve is shown in the present embodiment. The gage housing 348 can be releasably attached in the manner described herein to any of the above noted sleeves, regardless of size.

Parts List for FIGS. 1–19

10 blood pressure measuring device or apparatus
12 gage housing
12B gage housing
14 interior cavity
16 circumferential inner wall
18 open top end
19 reflexed portion
20 bottom end
20B bottom end
21 outer edge (support plate)
22 bubble or viewing window
24 downwardly extending portion
26 bottom opening
28 horizontal support plate
28A horizontal support plate
30 top facing side
32 bottom facing side
34 central through opening
36 sleeve
36A sleeve
36B sleeve
40 movement mechanism
42 diaphragm subassembly
44 diaphragm
44B diaphragm
45 circumferential ridge
46 O-ring
46B O-ring
47 outer edge
47B outer edge
48 pan
49 wave-like surfaces
49B wave-like surfaces
50 cavity
51 cavity
52 contact surface
53 lower end
54 axially displaceable shaft member
55 bottom end
56 tubular member
57 top end
58 top cap portion
59 end-ribbon spring
61 end-ribbon spring
62 indicating member
63 dial face
63A dial face
65 O-ring
66 threads
67 slot
68 biasing spring
68B biasing spring
69 recess
70 ribbon spring member
72 one end
73 threads
75 threads
80 slot
82 docking hub
114 circumferential slot
118 O-ring
140 gage or instrument housing
142 cuff
144 sleeve portion
146 sleeve portion
148 inner volume
152 upper housing portion
154 lower housing portion
156 intermediate portion
158 interior cavity
162 slot
165 support plate
166 detachable stethoscope adapter
167 dial face
170 arm
171 movement mechanism
174 extending attachment portion
176 port
178 hose
180 female connector
184 port
190 socket
194 instrument or gage housing
196 ball-shaped engagement end
198 direction
200 opening
202 peripheral bumper
206 ridge
210 gage housing
212 upper housing portion
214 movement mechanism
218 narrowed lower housing portion
220 engagement or mating end
222 socket
224 end opening
226 blood pressure sleeve or cuff
228 socket opening
232 rubberized peripheral guard or bumper member
234 stepped portion
236 gap
240 ribbon spring
242 axially displaceable shaft member
246 contained diaphragm
248 indicating member
250 circumferential channel
260 gage housing
264 upper housing portion
268 narrowed lower housing portion
270 engagement end
271 end opening
272 circumferential channel
274 movement mechanism
276 bottom surface
280 rubberized guard member
284 radially extending portion
285 rubberized shim
286 air gap
288 air gap
289 O-ring
290 axially extending portion
292 movement mechanism
294 gage housing
296 gage housing
297 threaded end
298 inlet port
299 bottom opening 300 port
302 cap
304 opening
305 tubular member
306 gage housing
307 pneumatic bulb
308 opening
309 output end
310 inlet port
320 socket
324 sleeve
328 interior
340 blood pressure measuring apparatus
344 sleeve
348 gage housing
352 barb or port
356 pneumatic bulb
360 tubing
364 check valve
368 sleeve portion
372 sleeve portion
375 patient
376 hook and loop fastener portion
380 artery index marker
384 indicia
388 indicia It will be readily apparent to those of ordinary skill in the field that other variations and modifications are possible within the spirit and scope of the invention as defined by the following appended claims.

We claim:

1. A blood pressure measuring device comprising:
a device housing having an upper portion and a lower portion, said lower portion including at least one engagement end that is directly couplable to an inflatable blood pressure sleeve to permit direct fluid communication between the interior of said device housing and the interior of said inflatable sleeve without hoses or tubing.

2. A pressure measuring device as recited in claim 1, wherein said engagement end includes at least one circumferential channel for reducing the transmission of shock or impact loads to a movement mechanism retained within said housing.

3. A pressure measuring device as recited in claim 2, wherein at least one circumferential channel is disposed on a bottom surface of said engagement end.

4. A pressure measuring device as recited in claim 2, wherein at least one circumferential channel is disposed along an axial portion of said engagement end.

5. A pressure measuring device as recited in claim 1, including said inflatable blood pressure sleeve, said sleeve having a receiving portion for directly receiving said engagement end, said receiving portion having an opening which permits fluid communication between the interior of the sleeve and the interior of the housing.

6. A pressure measuring device as recited in claim 1, including a movement mechanism disposed within said housing and shock absorbing means for preventing the transmission of certain shock and impact loads to the movement mechanism, said shock absorbing means including means for creating a discontinuous path for said shock and impact loads.

7. A pressure measuring device as recited in claim 6, wherein said shock absorbing means includes a peripheral bumper mount onto the exterior of said housing, said bumper having a periphery including at least one extending portion extending beyond said periphery, said extending portion including at least one gap region defining a buffer for absorbing a shock or impact load applied thereto.

8. A pressure measuring device as recited in claim 7, wherein said at least one extending portion of said peripheral bumper extends axially above a viewing window attached to said upper portion of said housing.

9. A pressure measuring device as recited in claim 7, wherein at least one extending portion of said peripheral bumper extends radially outward from the periphery of said bumper.

10. A pressure measuring device as recited in claim 6, wherein said shock absorbing means includes at least one circumferential channel in said lower portion.

11. A pressure measuring device as recited in claim 10, wherein said at least one circumferential channel is disposed in said engagement end.

12. A pressure measuring device as recited in claim 11, wherein said circumferential channel is cut into a bottom surface of said engagement end.

13. A pressure measuring device as recited in claim 11, wherein said circumferential channel is cut adjacent to a depending end of said engagement end.

* * * * *

UNITED STATES PATENT AND TRADEMARK OFFICE
CERTIFICATE OF CORRECTION

PATENT NO. : 6,796,186 B2 Page 1 of 1
DATED : September 28, 2004
INVENTOR(S) : Lia et al.

It is certified that error appears in the above-identified patent and that said Letters Patent is hereby corrected as shown below:

Column 16,
Line 21, change "mount" to -- mounted --.

Signed and Sealed this

Eighteenth Day of January, 2005

JON W. DUDAS
*Director of the United States Patent and Trademark Office*